United States Patent
Shoham

(10) Patent No.: US 12,103,166 B2
(45) Date of Patent: *Oct. 1, 2024

(54) DEVICE FOR IMPROVING THE ACCURACY OF MANUAL OPERATIONS

(71) Applicant: MAZOR ROBOTICS LTD., Caesarea (IL)

(72) Inventor: Moshe Shoham, Hoshaya (IL)

(73) Assignee: MAZOR ROBOTICS LTD., Caesarea (IL)

(*) Notice: Subject to any disclaimer, the term of this patent is extended or adjusted under 35 U.S.C. 154(b) by 951 days.

This patent is subject to a terminal disclaimer.

(21) Appl. No.: 17/021,723

(22) Filed: Sep. 15, 2020

(65) Prior Publication Data

US 2020/0406480 A1    Dec. 31, 2020

Related U.S. Application Data

(63) Continuation of application No. 13/390,500, filed as application No. PCT/IL2010/000667 on Aug. 17, 2010, now Pat. No. 10,828,786.

(Continued)

(51) Int. Cl.
    *B25J 17/02*    (2006.01)
    *A61B 17/16*    (2006.01)
    (Continued)

(52) U.S. Cl.
    CPC ....... *B25J 17/0216* (2013.01); *A61B 17/1675* (2013.01); *A61B 34/30* (2016.02);
    (Continued)

(58) Field of Classification Search
    CPC .. A61B 19/2203; A61B 2034/304–306; A61B 34/75–77; A61B 17/1622–1631;
    (Continued)

(56) References Cited

U.S. PATENT DOCUMENTS 6,238,384 B1    5/2001    Peer
6,535,794 B1    3/2003    Raab
(Continued)

OTHER PUBLICATIONS

"Robodoc" system supplied by Curexo Technology Corporation of Fremont CA, as disclosed in press release dated Oct. 30, 2008.
(Continued)

*Primary Examiner* — Rene T Towa
*Assistant Examiner* — H Q Nguyen
(74) *Attorney, Agent, or Firm* — Sheridan Ross P.C.

(57) ABSTRACT

A hand held robotic system that remains stiff so long as it is operating within allowed limits, but which become actively controlled once the operator exceeds those limits. The system thus corrects deviations by more than a predetermined amount of the operator's hand motions, so that the tool remains in the allowed region even when the operator's hand deviates from the planned trajectory. The pose and path of the robotic operating head is ascertained by means of a navigation or tracking system, or by means of a proximity device to measure the closeness of the operating head to a damage sensitive feature. As the tool deviates from its predetermined path or pose, or comes too close to the hazardous area, the robot control acts to move the tool back to its predetermined pose or path, or away from the hazardous region, independently of user's hand movement.

26 Claims, 4 Drawing Sheets

Related U.S. Application Data

(60) Provisional application No. 61/272,109, filed on Aug. 17, 2009.

(51) Int. Cl.
  *A61B 34/20* (2016.01)
  *A61B 34/30* (2016.01)
  *B25J 9/16* (2006.01)
  *A61B 17/00* (2006.01)
  *A61B 90/00* (2016.01)

(52) U.S. Cl.
  CPC ... *B25J 9/1676* (2013.01); *A61B 2017/00106* (2013.01); *A61B 2034/2055* (2016.02); *A61B 2034/304* (2016.02); *A61B 2090/061* (2016.02)

(58) Field of Classification Search
  CPC .......... A61B 34/30; A61B 34/70; A61B 2034/107–108; B25J 9/1676; B25J 9/1666; B25J 9/162–1623; B25J 17/0216
  See application file for complete search history.

(56) References Cited

U.S. PATENT DOCUMENTS

| | | | |
|---|---|---|---|
| 10,828,786 B2 * | 11/2020 | Shoham | B25J 9/1676 |
| 2002/0120188 A1 | 8/2002 | Brock et al. | |
| 2004/0128026 A1 | 7/2004 | Harris et al. | |
| 2005/0171553 A1 | 8/2005 | Schwarz et al. | |
| 2005/0182454 A1 | 8/2005 | Gharib et al. | |
| 2006/0142657 A1 | 6/2006 | Qaid et al. | |
| 2008/0161829 A1 | 7/2008 | Kang | |
| 2008/0228072 A1 | 9/2008 | Nycz et al. | |

OTHER PUBLICATIONS

The RIO™ Robotic Arm Interactive Orthopedic System, manufactured by Mako Surgical Corporation, Ft. Lauderdale, FL, USA, as disclosed in press release dated Feb. 24, 2009.
Ang et al. "Design and Implementation of Active Error Canceling in Hand-held Microsurgical Instrument," Proceedings of the 2001 IEEE/RSJ International Conference on Intelligent Robots and Systems, Oct. 29, 2001, vol. 2, No. 29, pp. 1106-1111.
Supplementary Search Report in corresponding European Patent Application No. 10809631.4, dated Sep. 1, 2016.
Examination Report for European Patent Application No. 10809631.4 corresponding to the present Application, dated Aug. 31, 2017.
Examination Search Report for Canada Patent Application No. 2,770,507 corresponding to the present Application, dated Aug. 1, 2016.
International Search Report and Written Opinion mailed Jan. 14, 2011 in PCT/IL2010/000667.
Official Action for U.S. Appl. No. 13/390,500, dated Aug. 1, 2013 7 pages Restriction Requirement.
Official Action for U.S. Appl. No. 13/390,500, dated Dec. 9, 2015 15 pages.
Official Action for U.S. Appl. No. 13/390,500, dated Feb. 24, 2017 15 pages.
Official Action for U.S. Appl. No. 13/390,500, dated Nov. 14, 2017 14 pages.
Official Action for U.S. Appl. No. 13/390,500, dated Jun. 28, 2018 15 pages.
Official Action for U.S. Appl. No. 13/390,500, dated Jan. 4, 2019 14 pages.
Official Action for U.S. Appl. No. 13/390,500, dated Oct. 3, 2019 18 pages.
Notice of Allowance for U.S. Appl. No. 13/390,500, dated Jun. 30, 2020 7 pages.
The Acrobot System Website, The Acrobot Company Limited, 2008, 2 pages [retrieved online from: web.archive.org/web/20090328131831/http://www.acrobot.co.uk/].

* cited by examiner

DEVICE FOR IMPROVING THE ACCURACY OF MANUAL OPERATIONS

CROSS REFERENCE TO RELATED APPLICATIONS

This application is a continuation of U.S. patent application Ser. No. 13/390,500, filed on Feb. 14, 2012, and entitled "Device for Improving the Accuracy of Manual Operations," which is a national stage application under 35 U.S.C. § 371 of PCT Application No. PCT/IL2010/000667, having an international filing date of Aug. 17, 2010, which designated the U.S., and which claimed the benefits of and priority under 35 U.S.C. § 119(e) to U.S. Provisional Application Ser. No. 61/272,109, filed on Aug. 17, 2009, entitled "Device for Improving the Accuracy of Manual Operations." The entire disclosures of each of the foregoing references is hereby incorporated herein by reference.

FIELD OF THE INVENTION

The present invention relates to the field of robotic correction of hand-directed tool operation, especially as applied to the correction of deviation from a preplanned surgical plan, or the correction of deviation from a targeted region by a surgeon or physician using a hand-held surgical tool.

BACKGROUND OF THE INVENTION

Numerous manual operations require high precision dexterity on the part of the operator to attain the required results. Such precision is not always attainable by the free human hand. One example where manual precision achieved by the operator may be of critical importance is in surgical orthopedic operations, in which the surgeon has to mill or drill a bone at a precise location and at a precise angle in order to fit a given implant to the subject's bone. Avoiding damage to vital anatomical features also requires high manual precision on the part of the surgeon. The orthopedic surgeon or neurosurgeon generally uses a saw, a drill or a milling tool in order to shape bones to create the required geometric profile. This is usually done free-hand, with the surgeon holding the surgical tool and following a trajectory based on anatomical landmarks. The accuracy of the orthopedic procedure is thus dependent on the skill of the surgeon in following the predetermined plan with the hand-held surgical tool.

Another example where the precision of the operator's manual dexterity may be a limiting feature occurs when targeting a point close to a sensitive anatomical structure, often for a procedure in soft tissue. Contact with the sensitive anatomical structure could be damaging to the subject. Examples of such procedures are in tumor removal, biopsy performance, precise drug delivery, and others. Currently, proximity sensors or various imaging methods can be used to detect hazardous features such as blood vessels or nerves close to the target area. A warning such as a visual or audible signal can be issued to the surgeon or physician if, when aiming for the target area, the hazardous feature is approached by a predetermined distance. Techniques such as Doppler ultrasound flow detection can be used to detect blood vessels by the flow of blood therein, and neuro-monitors can be used to detect the presence and position of nerve structures. In order to warn the surgeon or physician of the presence of such a structure, and the danger of damaging it, a proximity warning is provided when the potentially damaging surgical tool is at a predetermined safety margin from the structure. Even though the real-time sensor provides a visual or audio warning signal when approaching the forbidden zone, reliance is still laid on the dexterity of the surgeon or physician to avoid damage, such that the predetermined safety margin is generally chosen conservatively, to avoid potential damage.

The introduction of computer-assisted surgery enables tracking of the position of the surgical tool relative to the bone, so that more accurate bone shaping or drilling can be achieved. A number of different approaches exist in the prior art using such computer-assisted surgery.

In the Robodoc® system supplied by Curexo Technology Corporation of Fremont CA, for example, a robot holds and maneuvers the surgical tool based on data from a preoperative plan. This results in more accurate bone shaping that enables, for instance, better fitting of hip implants. In such an active system, the entire milling operation procedure is executed by the robot, without the need for the surgeon to manipulate the tool, such that it can be said that the actual surgical operation is done by the robot. Thus although the result is generally very accurate, the system is large and costly, such that its use has been limited.

Another approach to bone shaping is to control the surgical tool while it is held "simultaneously" by the surgeon and the robot. The tool is held by the robotic arm, most conveniently at its upper extremity, so that the surgeon can hold the main part of the tool's body using a natural grip without impedance from the robotic arm. So long as the tool is within the allowed region of operation, as defined by the preoperative plan, the robot is transparent to the surgeon's hand motion, and allows the surgeon to perform the manual operation he intends. However, the moment that the surgeon's hand strays beyond of the permitted limits of operation, the robot control detects this departure, and stiffens the joints to physically block the tool. This procedure is called the "active constraint" approach, in which the tool is manipulated by the surgeon, but is blocked by the robot when moved beyond the allowed region. Two commercial systems are currently available, using this approach for shaping of the knee joint—the Acrobot system (www.acrobot.co.uk) manufactured by Acrobot Ltd., of London, El, U.K., and the Rio system (www.makosurgical.com), manufactured by Mako Surgical Corporation, of Ft. Lauderdale, Fl, U.S.A. Alternatives to the "active constraint" approach are those that apply a control to the surgical tool itself, such as stopping its operation, or retracting the milling or cutting head from the forbidden zone, such as in system supplied by Blue Belt Technologies Inc. of Pittsburgh, PA.

The disclosures of each of the publications mentioned in this section and in other sections of the specification, are hereby incorporated by reference, each in its entirety.

SUMMARY OF THE INVENTION

In contrast to the above mentioned "active constraints" approach that keeps the robot as transparent to the surgeon as possible within the allowed region, and as stiff as possible once the surgeon exceeds the allowed limits, the present disclosure proposes a robotic system that remains stiff and hence inoperative so long as the surgeon is operating within the allowed region, but which become actively controlled once the surgeon exceeds the allowed limits and enters a forbidden region. The hand-held robot thus corrects the surgeon's free hand motions and compensates for their deviations, so that the tool remains in the allowed region or follows the pre-planned path even when the surgeon's hand deviates from the planned trajectory more than the predetermined allowance. The pose and path of the robotic operating head is ascertained in real time by means of a navigation or tracking system, or by use of an imaging system with signal processing capability to define the pose of the robotic operating head, used to determine the real time positions of the head or the tool born by the head and of the body part on which the tool is operating.

Alternatively, the position of the robotic operating head is determined by means of a proximity device to measure the closeness of the operating head to a damage sensitive feature, such as a blood vessel, a nerve, a sensitive region of the brain, a bodily organ, or other areas the surgeon wants to avoid. As the tool deviates from its preoperatively determined path or pose, or comes too close to the hazardous area, the robot control comes into action to move the tool back to its predetermined pose or path, independently of the pose or path of the operating head defined by the grip of the surgeon, thus compensating for the errors in the path or pose chosen by the surgeon.

This suggested system has several advantages over the prior art active constraint systems, as there is no need for a large robot that holds in parallel both the surgical tool and the mechanical control mechanism that makes the robot motion transparent within the allowed region and stiff at the borders of the allowed region.

One exemplary implementation involves a robotic system comprising:
 (i) a hand held robotic operating head comprising:
  (a) a gripping body adapted to be held by the operator, and
  (b) a robot having a base and a robotically controlled platform, the base being attached to the gripping body, and the robotically controlled platform bearing an operating tool, and
 (ii) a detection system adapted to relate the position of the operating tool relative to a region of an object where the operating tool is forbidden to operate,
 wherein the robot is adapted to use an output from the detection system to change the pose of the robotically controlled platform if the gripping body deviates by a amount which would cause the operating tool to operate in the forbidden region.

In such a system, the region where the operating tool is forbidden to operate may be a region in which the operating tool deviates by more than a predetermined amount from a preset path of operation, or alternatively, a region which deviates more than a predetermined amount from a surgical plan for execution on a subject. The operating tool may be a surgical tool for performing an orthopedic operation on a bone of the subject.

Other implementations may further involve a robotic system as described above, wherein the detection system comprises a tracking system which detects the pose of at least one of the gripping body, the robotically controlled platform, the operating tool and the object containing the region in which the operating tool is forbidden to operate.

Additionally, alternative implementations of the above-described robotic system may further be such that the region where the operating tool is forbidden to operate is a region which is closer by more than a predetermined distance from a feature which may be damaged by the operating tool. In such a case, the operating tool may be forbidden to operate in a region which deviates more than a predetermined amount from a surgical plan for execution on a subject. Alternatively, the operating tool may be a surgical tool for performing a surgical procedure in soft tissue close to a damage sensitive organ of a subject. Examples of such a damage sensitive organ include a nerve, a blood vessel, a bodily organ, and a sensitive region of the brain. The surgical tool may then be any one of a biopsy needle, a drug delivery needle, and a scalpel, and the surgical procedure may be any one of tumor removal, biopsy performance, and drug delivery.

Such systems where the operating tool is forbidden to operate in a region which is closer by more than a predetermined distance from a feature which may be damaged, may involve use of a detection system comprising a proximity sensor for determining the distance of the operating tool to the damage sensitive area. The proximity sensor may then comprise either of an ultrasound Doppler blood flow sensor, or a neural monitor.

Yet other implementations of the robotic system may comprise:
 (i) a hand held robotic operating head comprising:
  (a) a gripping body adapted to be held by the operator, and
  (b) a robot having its base attached to the gripping body, and bearing an operating tool on its robotically controlled platform,
 (ii) a tracking system to register the hand held robotic operating head with an object on which the operating tool is to operate, and
 (iii) a controller adapted to change the pose of the robotically controlled platform if the gripping body deviates by more than a predetermined amount from a predetermined path of operation on the object.

In such a robotic system, the object on which the operating tool is to operate may be a subject's bone, and the operating tool is then a surgical tool for performing an orthopedic operation on the bone. The tracking system may comprise a tracker head mounted on the object on which the operating tool is to operate and a tracking target mounted on at least one of the gripping body of the robotic operating head or the robotically controlled platform. Alternatively, the tracking system may comprise a tracker head mounted on at least one of the gripping body on the robotic operating head or the robotically controlled platform, and a tracking target mounted on the object on which the operating tool is to operate.

Further example implementations involve a robotic system comprising:
 (i) a hand held robotic operating head comprising:
  (a) a gripping body adapted to be held by the operator, and
  (b) a robot having its base attached to the gripping body, and bearing an operating tool on its robotically controlled platform,
 (ii) a position detection system to relate the proximity of the operating tool to an object which the operating tool is forbidden to approach by a predetermined distance, and
 (iii) a controller adapted to change the pose of the robotically controlled platform if the gripping body deviates by an amount which would cause the operating tool to approach the object by less than the predetermined distance.

In such a robotic system, the object may be a damage-sensitive feature of a subject. This feature could be any one of a blood vessel, a nerve, a bodily organ or a sensitive brain section. The position detection system could be a proximity sensor.

Although the system is described in this disclosure is applicable to a surgical environment, it is understood that the system is not intended to be limited to surgical use, but can also be used for other non-medical applications, such as scribing, three dimensional modeling, and the like.

BRIEF DESCRIPTION OF THE DRAWINGS

The present invention will be understood and appreciated more fully from the following detailed description, taken in conjunction with the drawings in which.

DETAILED DESCRIPTION

Figure 1:
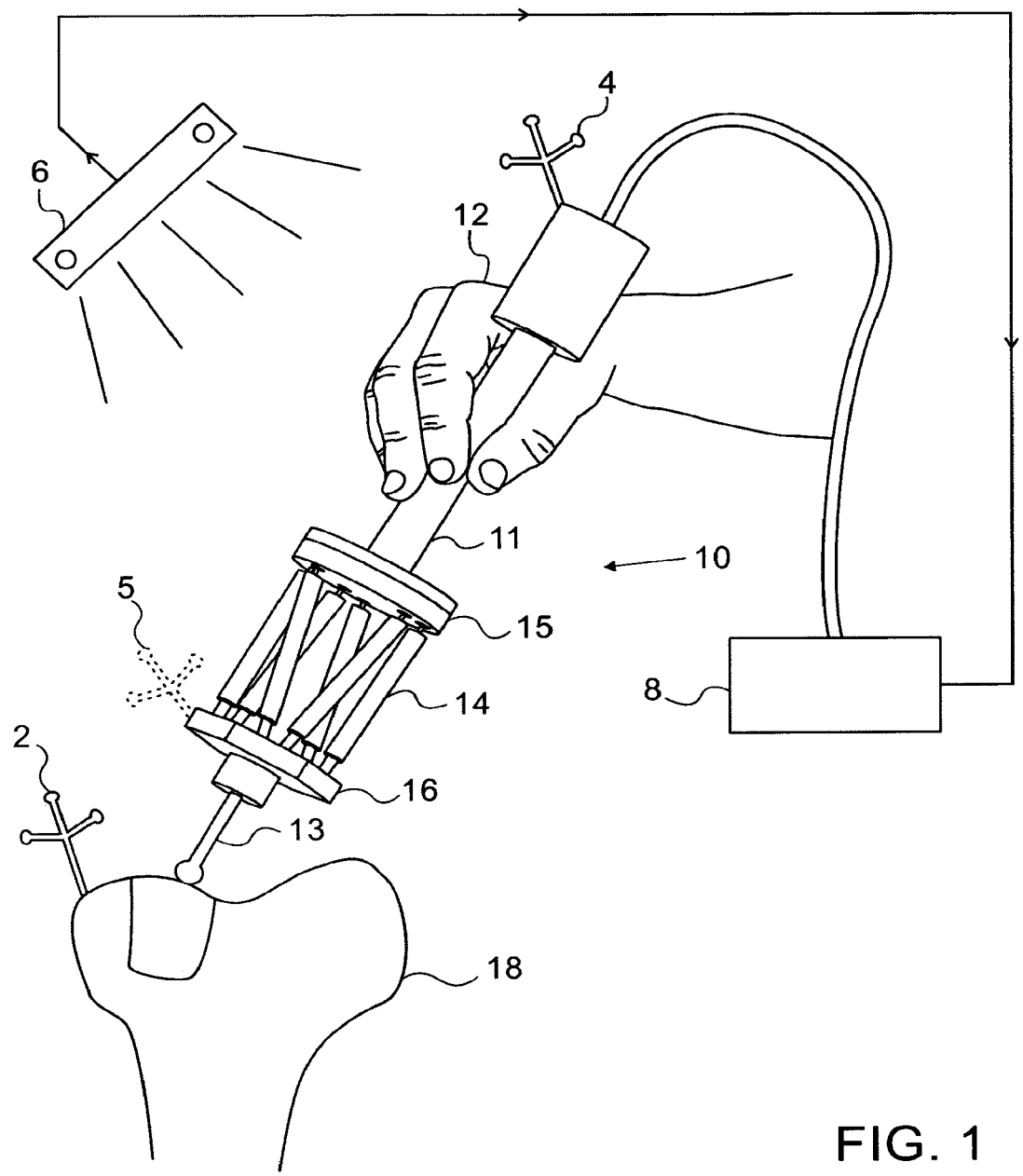
FIG. 1 shows an exemplary hand-held robotic surgical system as described in this disclosure, for shaping a subject's bone.

Reference is now made to FIG. 1 which illustrates an exemplary hand-held robotic system using the principle described hereinabove. The system described herewithin is a surgical system, illustrated here for shaping a bone, but it is to be understood that this is only one exemplary application of such a system and it can equally well be used for other applications where a hand guided operation is to be controlled to ensure that the operator does not deviate from predetermined bounds. Another such example is shown hereinbelow.

The robotic system includes a hand held robotic operating head 10, which is constructed of two parts. An upper part 11 is in the form of a gripping handle which is shaped so that it can be comfortably held in the hand 12 of the surgeon performing the operation. The surgeon uses a preoperative plan to decide in which pose (spatial position and angular orientation) to hold the head and which path to follow. Whereas in prior art surgical operating heads, the operating tool, whether a drill, a milling head, or any other surgical tool would be connected directly to the gripping handle, in this system, the tool 13 is connected to the gripping handle, and hence to the surgeon's hand, only through a controlled robot 14. The base 15 of the robot is attached to the gripping handle 11, while the operating tool 13 is held in the robotically controlled platform 16 of the robot. The robot can be of any type, and is illustrated in this disclosure as a Stewart-Gough parallel robot type, which has 6-extendible operating links between the base and the moveable platform. Such a robot is used to illustrate the implementation shown in the drawings and it clearly shows the operating action of the robot to correct the surgeon's deviation from the allowed path. However, it is to be understood that the robotic structure used can be of any suitable type, and in particular, a robot with actuating motors incorporated within the handle above the output platform may provide a more compact configuration. Compact dimensions are an important characteristic for such a hand-held application.

In FIG. 1, the operating head 10 is shown being used by the surgeon in a unicodyler knee replacement procedure, to mill the surface of a bone 18 with the operating tool 13, so that the milled bone head matches a preselected unicompartmental implant. Preoperatively the surgeon has planned the optimal location of the implant, and from this plan, the milled shape of the knee surface is calculated. This shape is input to the controller 8 as the preoperative plan which the surgeon has to adhere to accurately in order to ensure compliance with the planned operation, and hence a good fit of the implant on the bone.

A tracking system is used intra-operatively, to enable dynamic referencing of the bone 18 on which the operation is being performed with the robotic operating head 10. This is performed in order to link the locations of the bone and the robotic operating head 10 to the same coordinate system, so that movements of the robotic operating head can be correlated with the position of the bone. The tracking system may utilize a tracker 6 surveilling the operating site, and determining the pose of the robotic operating head 10 and of the subject's bone 18 by means of referencing targets 2, 4, attached to these items. If an optical tracking system is used, the referencing targets may conveniently be constructed of a plurality of light emitting diodes (LEDs) arranged in a predetermined pattern. The tracker 6 may then include optical sensors which are able to determine the pose of the referencing targets, such as by means of triangulation. Alternative configurations may include the use of retro-reflectors in the referencing targets 2, 4, in which case the tracker 6 would include both the light emitting sources (usually LED's) and the detectors for receiving the light retro-reflected from the referencing targets. Additionally, trackers are now available which operate in a completely passive mode, requiring no light emitting sources, and relying solely on high reflection coatings on the referencing targets, to reflect the ambient light to the tracker detector 6. The tracking system transfers the positional data relating to the robotic operating head and to the bone to the system controller 8, which also contains the preoperative plan data. Although the system has been described herewithin using optical tracking, it is to be understood that any other form of tracking may be equally well used, such as RF, sonic, ultrasonic or magnetic tracking or even a contact tracker like a digitizer.

As long as the surgeon manipulates the robotic operating head such that the surgical tool 13 follows the preoperative plan within an allowed deviation region, as ascertained by the tracker inputs to the system controller, the robot 14 remains locked and the entire robotic operating head 10 is manipulated as one rigid body. Once the surgeon deviates from the allowed path or pose, this deviation is detected by the tracked position of the referencing target 4 on the robotic operating head 10, and the controller is programmed to send a correction signal to the robot 14 to alter its pose, such that the tool tip 13 is brought back into the allowed region, even though the surgeon's hand has directed the robotic operating head 10 beyond those limits.

Figure 2:
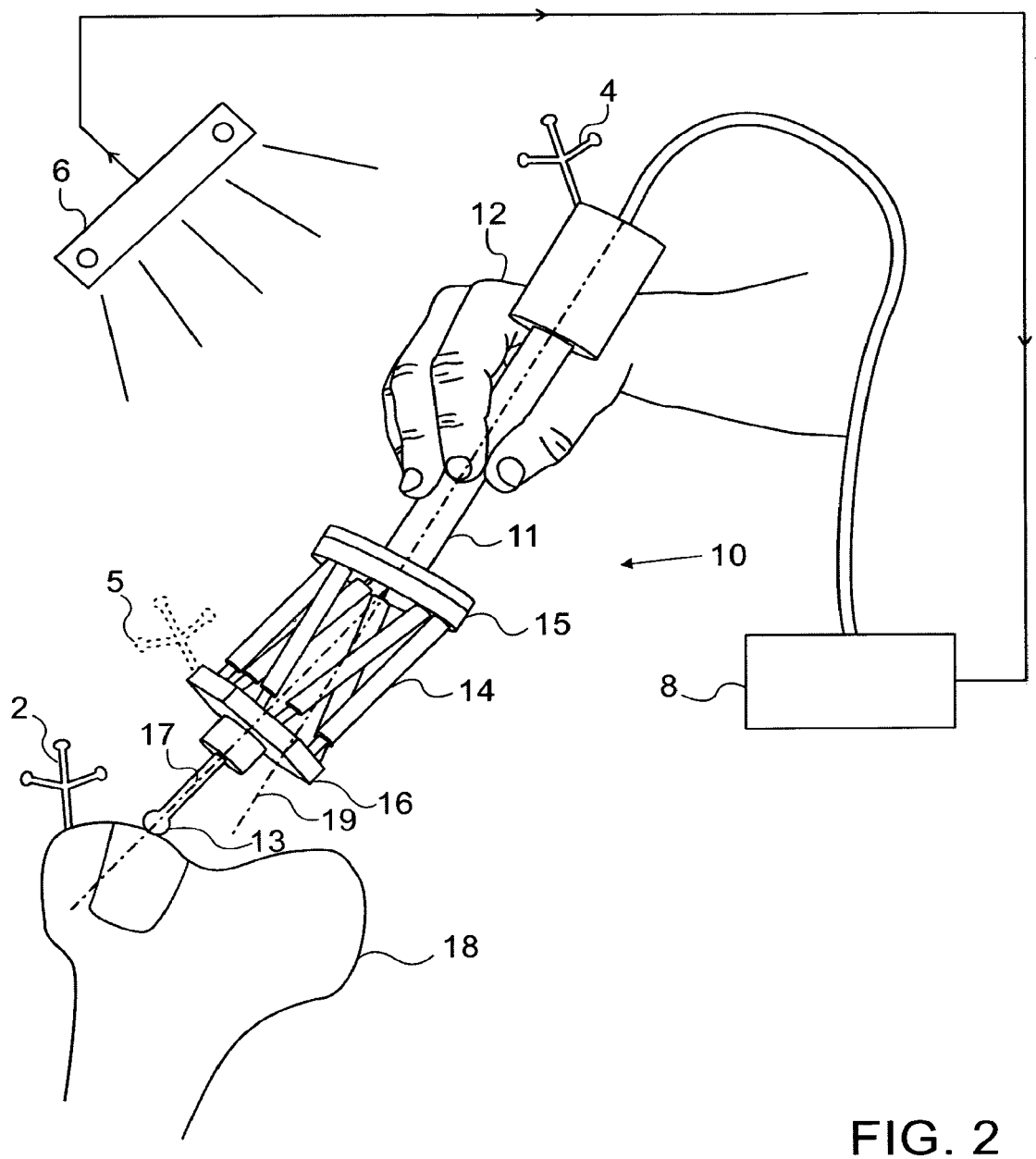
FIG. 2 shows the operation of the robotic controller in correcting for deviation of the surgeon's hand from a predetermined surgical plan for shaping of the bone.

This situation is shown in FIG. 2, where it is seen that the surgeon's hand 12 has deviated, as shown by the axis 19 of the hand grip, from the angle which would maintain the axis 17 of the cutting tool 13 in the correct position and pose relative to the bone 18. However, this deviation has been sensed by the navigation 6 and control system 8, and the pose of the robot 14 has been changed in order to maintain the cutting tool 13 in the correct position and pose relative to the bone 18, despite the surgeon's hand deviation.

The robot 14 thus compensates for the surgeon's deviation and provides accurate compliance with the preoperative plan. In order to accomplish this successfully, the robot must react in real-time, which means that the system should have a response time sufficiently short that even with the most rapid movement the surgeon may make, the system will correct departure from the allowed preoperative plan before any damage is done. Typically, this means that the system should have a response bandwidth of the order of at least 10 Hz in order to follow the fastest human hand movements expected in such operations. Furthermore, the surgeon should not make movements much further from the allowed region that would cause the robot to exceed its working envelope. In general, both of these limitations should be achievable with the available robotic actuating motors and robotic control systems. The robotic actuators used can be of any type that can supply the required forces and the required speed, such that not only suitable electro-magnetic motors but also piezoelectric, hydraulic or pneumatic actuators may be used.

Furthermore some warning signal may be incorporated in the system, to advise the surgeon when his hand motion approaches the borders of the allowed region of operation according to the preoperative plan. Such a warning signal may be generated by the robot control, and could also be graduated, such as in intensity, tone or frequency, to indicate the extent of deviation of the surgeon from the preoperative plan. Possible implementations of this warning signal could be by an audible signal, or by a visual signal, or by some form of tactic feedback provided by the robot to the surgeon's hand.

Figure 3:
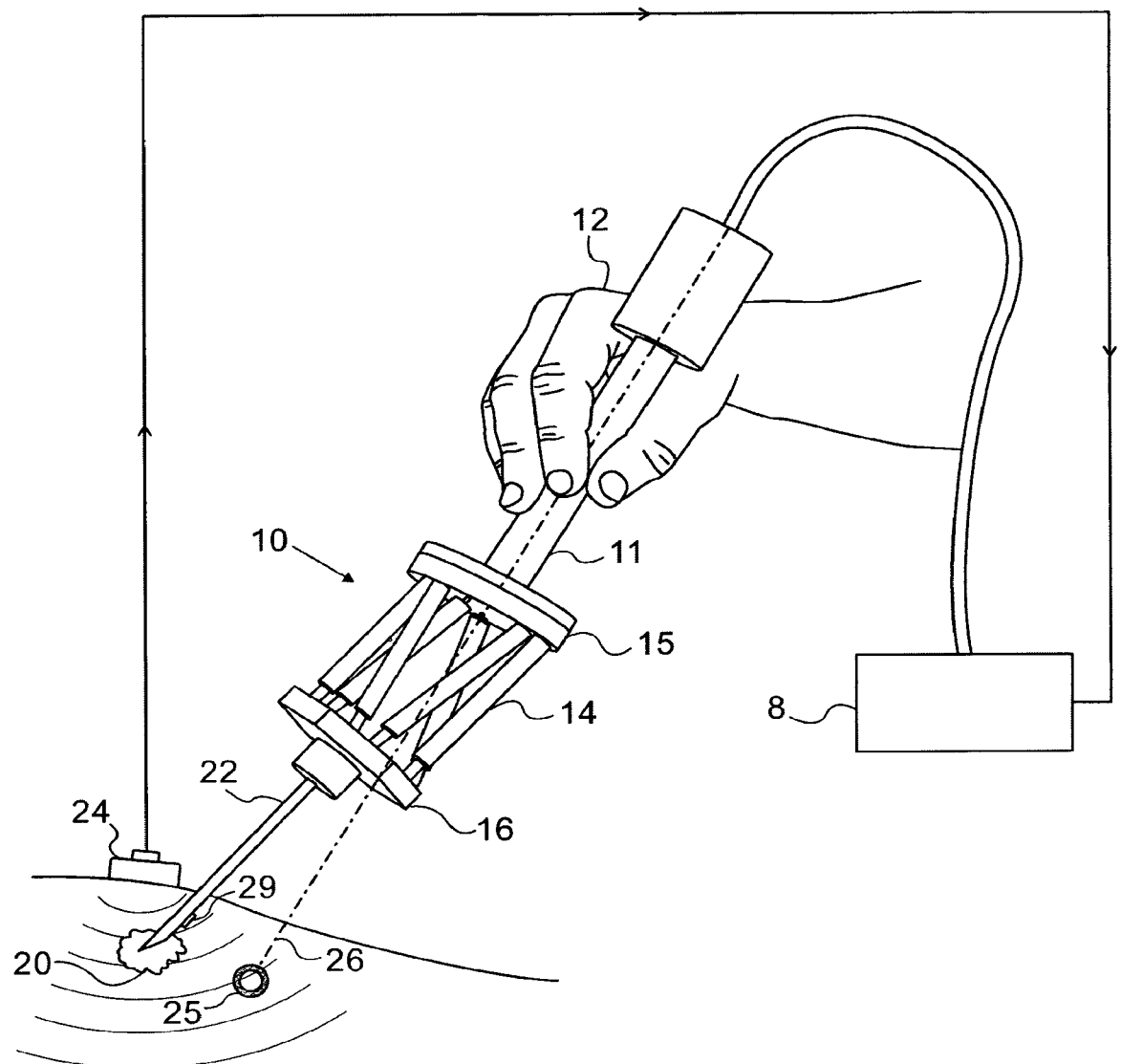
FIG. 3 shows an application of the hand-held robot of FIG. 1, for performing a targeted procedure in soft tissue of a subject close to a sensitive anatomical structure.

Reference is now made to FIG. 3, which shows an additional exemplary application of the hand-held robot of FIG. 1, for performing a targeted procedure in a region 20 of soft tissue of a subject close to a sensitive anatomical structure, such as a nerve or a critical blood vessel 25. Contact with the sensitive anatomical structure could be damaging to the subject. Examples of such a procedure could be in tumor removal, biopsy performance, precise drug delivery, and others. The surgeon or physician can be warned of the presence of the hazardous feature either by an imaging system, such as a fluoroscopic system or by an ultrasonic imaging system, a probe of which 24 is shown in FIG. 3, or by means of a proximity sensor 29 attached to the needle 22 or surgical tool, which provides a warning signal when the sensor approaches the hazardous feature by a predetermined distance. Techniques such as Doppler ultrasound flow detection can be used to detect blood vessels by the flow of blood therein, and neuro-monitors can be used to detect the presence and position of nerve structures. The proximity sensor can advantageously deliver its warning signal by radio transmission to the control unit 8. Even for open surgical procedures, where the surgeon or physician could see the damage-sensitive feature, the robotically controlled system of this disclosure enables him to perform the desired procedure close to the damage-sensitive feature without fear that he will cause damage to the feature by a careless and unintentional movement of the hand.

Either the imaging system or the proximity sensor provides a signal input to the control system 8, which then provides a feedback to the robot 10 to prevent the needle 22 or surgical tool from approaching the sensitive feature, even if the surgeon or physician's hand movement would have directed it to do so. This is illustrated in FIG. 3, where, although the axis 26 of the handle would have directed the needle 22 straight at the blood vessel 25, the robotic control has changed the pose of the robot so as to divert the needle away from the blood vessel 25 and back to its intended target 20. This implementation differs from that shown in FIG. 2, in that the control system does not limit the operating head to operation within a predefined envelope, but rather prevents the operating head from getting too close to a forbidden region of operation. However, both implementations share the common feature that the robotic control uses a warning signal provided by a position detection system in order to prevent the operating head from operating in a region where the operator's hand movement would have directed it to do so.

The use of this robotic compensation system has the advantage over prior art free-hand manual proximity warning systems in that the accuracy of the procedure can be increased compared to that of prior art systems having no active control of the surgeon's hand position. It is possible to provide greater precision and thus to operate closer to hazardous locations than using manual proximity warning systems, and thus to achieve a better operational result.

Figure 4:
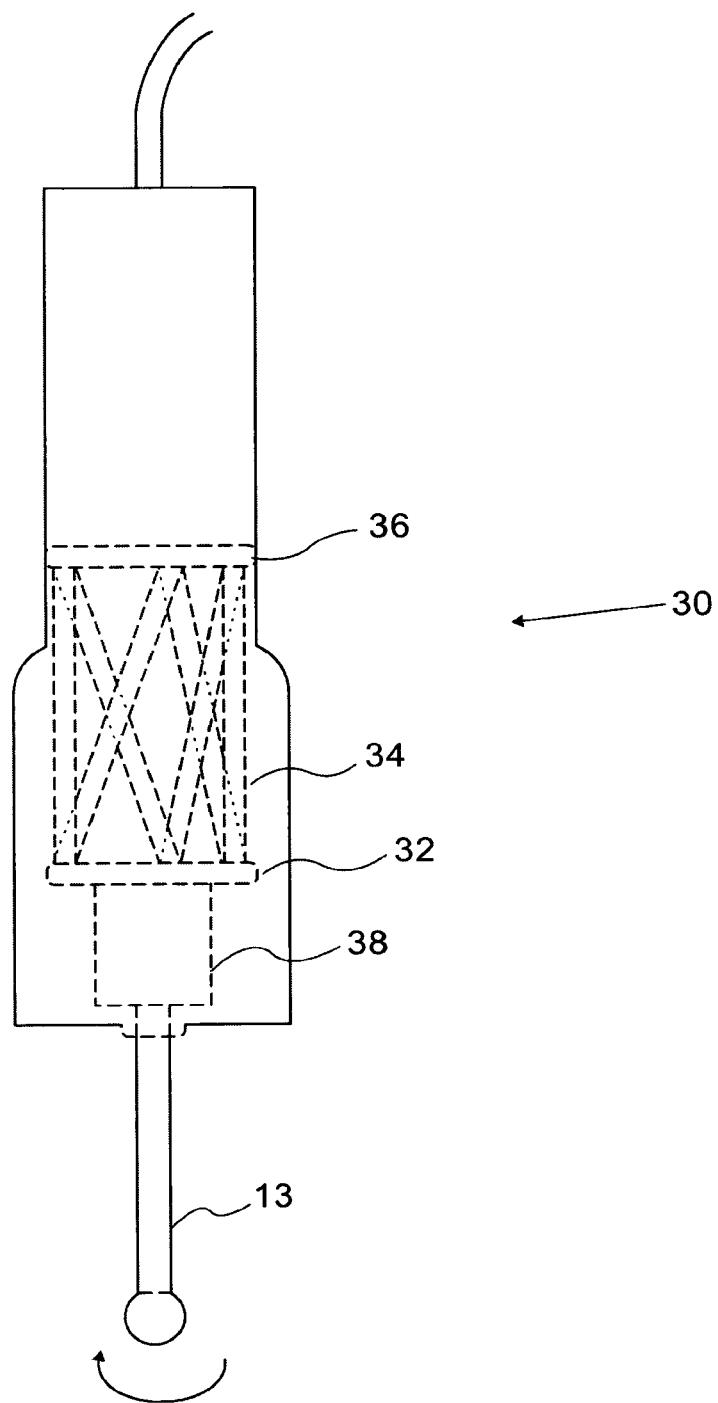
FIG. 4 shows an exemplary compact robotic operating head for hand held use by the surgeon.

Reference is now made to FIG. 4, which shows a schematic cut-away representation of a complete robotic operating head 30 with a robot of sufficiently compact design that it can be incorporated into the body profile of the head. The head thus becomes much more compact and readily handled by the surgeon than that shown schematically in FIGS. 1 to 3. A schematic outline of a robot is shown in dotted lines within the body of the head. The surgical tool 13, shown in the example of FIG. 4 with a milling bur on its working extremity may be rotated by means of a motor 38 mounted on the moving platform 32 of the robot, or by a shaft driven by a motor located remotely. If the tool is of the type that does not require motion, such as scalpel ablation, coagulation, laser cutting, or similar procedures, the need for providing motion to the tool is obviated. The moving platform 32 may be actuated by means of robotically actuating arms 34 which are affixed at the end remote from the driven platform to the robotic base, 36, which is fixed relative to the complete robotic operating head 30. As previously mentioned, any other suitable robot structure may equally well be used, with its base attached to the robotic operating head 30 and with its driven output element bearing the surgical tool.

For those implementations using a tracking system, the set-up described in FIG. 1 illustrates only one possible arrangement by which the mutual motion of the robotic operating head 10 and the bone 18 are correlated. As an alternative to, or in addition to the tracking target 4 mounted on the gripping part 11 of the robotic operating head 10, a tracking target 5 can be mounted on the robotic moving platform 16 of the robot 14, such that the actual position of the surgical tool 13 is tracked directly. Since the system controller 8 knows the pose of the robot 14 and hence the positional relation between the gripping portion 11 of the robotic operating head and the surgical tool 13, the use of both of these tracking targets 4, 5, provides a level of redundancy which may be used for increasing the safety of the system.

Since both the bone and the robotic operating head are situated very close to each other, it may be disadvantageous to use a conventional external navigating or tracking system, which is generally disposed above the operating table and at some distance from the operating site, with its concomitant problems of accuracy at such a distance, and of the need to maintain a clear line of sight between the tracker and the tracking targets. According to an alternative implementation of the present system, the tracking could advantageously be performed locally, such as by mounting the tracker on the bone 18 and the tracking target or targets on the robotic operating head, either on the gripper part 11 or on the robotically directed tool holder platform 16, or on both, or vice versa with the tracker on the robotic operating head (whether the gripper part 11 or the moveable platform 16, or on both) and a tracking target on the bone 18.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

I claim:

1. A surgical system comprising:
   a handheld robotic operating head comprising:
      a first part comprising a platform and a robotic mechanism, the robotic mechanism configured to selectively move the platform, and the platform being configured to bear an operating tool; and
      a second part comprising a handle and a base, wherein the base is positioned between the robotic mechanism and the handle, and wherein the handle enables an operator's hand to grip and maneuver the robotic operating head; and
   a controller that controls the robotic mechanism according to a signal received from a tracking system, the signal corresponding to a position of the operating tool relative to an allowed region, wherein:
      (i) when the signal indicates that the operating tool is within the allowed region, the robotic mechanism remains in an inactive rigid mode in which the robotic mechanism does not move the platform relative to the base and the handle; and
      (ii) when the signal indicates that the operating tool has reached a forbidden region, the controller automatically causes the robotic mechanism to move the platform relative to the base and the handle such that the operating tool remains in the allowed region.

2. The surgical system of claim 1, further comprising a motor that drives the operating tool, and wherein, in (ii), the controller causes the robotic mechanism to move the platform relative to the base and the handle to maintain an axis of the operating tool while an axis of the base and the handle varies, to keep the operating tool in the allowed region.

3. The surgical system of claim 1, wherein the forbidden region corresponds to at least one damage-sensitive anatomical element.

4. The surgical system of claim 3, wherein the tracking system comprises a proximity sensor for determining a distance of the operating tool from the damage-sensitive anatomical element.

5. The surgical system of claim 4, wherein the proximity sensor comprises a blood flow sensor or a neural monitor.

6. The surgical system of claim 1, wherein the tracking system detects the position of at least one of the platform or the operating tool.

7. The surgical system of claim 1, further comprising a tracking target mounted to at least one of a body of the operating head or the platform.

8. The surgical system of claim 1, wherein the forbidden region corresponds to a predetermined distance from a pre-set path of operation.

9. The surgical system of claim 1, wherein the operating tool is a surgical tool for performing a surgical procedure in soft tissue, or for performing an orthopedic operation on a bone.

10. The surgical system of claim 1, wherein the tracking system comprises a tracker secured to the operating head.

11. A surgical compliance system comprising:
   a handheld robotic operating head comprising a base connected to a platform by a robotic mechanism, the robotic mechanism configured to selectively move the platform relative to the base, the platform being configured to bear an operating tool, the handheld robotic operating head being such that an operator can free-handedly manipulate the entire robotic operating head; and
   a controller configured to autonomously switch the robotic mechanism between a mechanically inactive state in which the platform remains in a fixed position relative to the base, and a mechanically active state in which the robotic mechanism moves the platform relative to the base,
   wherein the controller switches the robotic mechanism into the mechanically active state when the operating tool deviates by more than a predetermined distance from a predetermined path of operation.

12. The surgical compliance system of claim 11, wherein the controller switches the robotic mechanism back into the mechanically inactive state when the operating tool no longer deviates by more than the predetermined distance from the predetermined path of operation.

13. The surgical compliance system of claim 11, wherein the controller receives a signal from a tracking system corresponding to a distance of the operating tool from the predetermined path of operation.

14. The surgical compliance system of claim 13, wherein the tracking system comprises a proximity sensor.

15. The surgical compliance system of claim 13, wherein the tracking system utilizes a tracking target secured to at least one of the platform or a body of the operating head.

16. A surgical safety system comprising:
   a handheld robotic operating head comprising a base connected to a platform by a robotic mechanism, the robotic mechanism configured to selectively move the platform relative to the base, the platform being configured to bear an operating tool, the base configured to be supported and moved solely by an operator;
   a position detection system generating an output relating a position of the operating tool relative to an allowed operation region; and
   a controller adapted to use the output to autonomously switch the robotic mechanism between an operator controlled state, in which the platform remains in a fixed position relative to the base, and a robotically controlled state, in which the robotic mechanism changes the position of the platform relative to the base to maintain the operating tool within the allowed operation region.

17. The surgical safety system of claim 16, wherein the allowed operation region is defined by a preoperative plan.

18. The surgical safety system of claim 16, further comprising a motor that drives the operating tool.

19. The surgical safety system of claim 16, wherein the operating tool is a biopsy needle, a drug delivery needle, or a scalpel.

20. The surgical safety system of claim 16, wherein the system has a response bandwidth of at least 10 Hz.

21. A surgical robotic system, comprising:
   a robotic operating head comprising:
      a first part comprising a platform and a robotic mechanism, the robotic mechanism being configured to selectively move the platform, the platform being configured to engage a surgical tool; and
      a second part comprising a handle and a base, wherein the base is positioned between the robotic mechanism and the handle, and wherein the handle enables an operator's hand to grip and maneuver the robotic operating head; and a controller that controls the robotic mechanism according to one or more signals received from a tracking system, the tracking system comprising:
- a tracking target configured to be mounted on an external object and to indicate a pose of the external object when mounted thereon; and
- a tracker head mounted on the robotic operating head, the tracker head configured to detect the tracking target and enable the tracking system to provide information regarding a pose of the surgical tool relative to the external object, wherein the one or more signals are indicative of a position of the surgical tool relative to an allowed region, wherein:
(i) when the one or more signals indicate that the surgical tool is within the allowed region, the robotic mechanism remains in an inactive rigid mode in which the robotic mechanism does not move the platform relative to the base and the handle; and
(ii) when the one or more signals indicate that the surgical tool has reached a forbidden region, the controller automatically causes the robotic mechanism to move the platform relative to the base and the handle such that the surgical tool remains in the allowed region.

22. The surgical robotic system according to claim 21, wherein the external object is a bone of a patient and the surgical tool is configured to operate on the bone.

23. The surgical robotic system according to claim 22, wherein a proximity of the tracker head to the tracking target enables the tracking system to provide the information while reducing line of sight issues between the tracker head and the tracking target.

24. The surgical robotic system according to claim 22, wherein a proximity of the tracker head to the tracking target enables the tracking system to provide the information, the information having a higher accuracy than corresponding pose information from a system having a remote tracker head.

25. The surgical robotic system according to claim 21, wherein the tracker head is mounted on the platform.

26. The surgical robotic system according to claim 25, wherein the platform forms part of a distal end portion of the robotic mechanism.

* * * * *